US012599476B2

(12) United States Patent      (10) Patent No.:    US 12,599,476 B2

Matz et al.                 (45) Date of Patent:      Apr. 14, 2026

(54) AI-BASED VIDEO ANALYSIS OF CATARACT SURGERY FOR DYNAMIC ANOMALY RECOGNITION AND CORRECTION

(71) Applicant: Carl Zeiss Meditec AG, Jena (DE)

(72) Inventors: Holger Matz, Unterschneidheim (DE); Stefan Saur, Aalen (DE); Hendrik Burwinkel, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 963 days.

(21) Appl. No.: 17/659,794

(22) Filed: Apr. 19, 2022

(65) Prior Publication Data

US 2022/0331093 A1     Oct. 20, 2022

(30) Foreign Application Priority Data

Apr. 20, 2021    (DE) ..................... 10 2021 109 945.5

(51) Int. Cl.
    *G06N 20/00*       (2019.01)
    *A61F 2/16*        (2006.01)

(52) U.S. Cl.
    CPC .......... *A61F 2/1627* (2013.01); *A61F 2/1618* (2013.01); *G06N 20/00* (2019.01)

(58) Field of Classification Search
    CPC ........ A61F 2/1627; A61F 2/1618; A61F 2/16; A61F 9/00736; G06N 20/00; G06N 3/044; G06N 3/0464; G06N 3/09; G06N 3/084; A61B 3/145; A61B 90/20; A61B 3/0025; G16H 20/40; G16H 30/20; G16H 30/40; G16H 50/20; G16H 50/70
    See application file for complete search history.

(56) References Cited

U.S. PATENT DOCUMENTS

| | | | | |
|---|---|---|---|---|
| 2015/0103313 A1* | 4/2015 | Sarver | .................. | A61B 3/1015 |
| | | | | 351/205 |
| 2017/0290502 A1* | 10/2017 | Linder | ................. | A61B 3/0025 |
| 2019/0110753 A1* | 4/2019 | Zhang | ................. | A61B 3/0025 |
| 2021/0313052 A1* | 10/2021 | Makrinich | ............ | G11B 27/34 |

FOREIGN PATENT DOCUMENTS

JP         2022051166 A     3/2022

OTHER PUBLICATIONS

Japanese Notice of Reason for Refusal for the related Application No. JP2022051166A, dated May 31, 2023, 3 pages.

* cited by examiner

*Primary Examiner* — Sanchita Roy
(74) *Attorney, Agent, or Firm* — Honigman LLP; Brett A. Krueger

(57) ABSTRACT

A computer-implemented method for recognizing deviations from plan parameters during an ophthalmological operation is described, the method including: providing video sequences of cataract operations, the video sequences having been recorded by means of an image recording apparatus, training a machine learning system using the video sequences provided and also, in each case, a planned refractive power of an intraocular lens to be inserted during a cataract operation and a target refraction value following the cataract operation as training input data and associated prediction results in the form of an actual refraction value following the cataract operation to form a machine learning model for predicting the actual refraction value following the cataract operation, and persistently storing parameter values of the trained machine learning system.

20 Claims, 6 Drawing Sheets

400

402

406   404

312 Trained machine learning system

408 Visualizing the predicted target refraction value following the operation, actual refraction value following the operation, a deviation value, etc.

Figure 1:
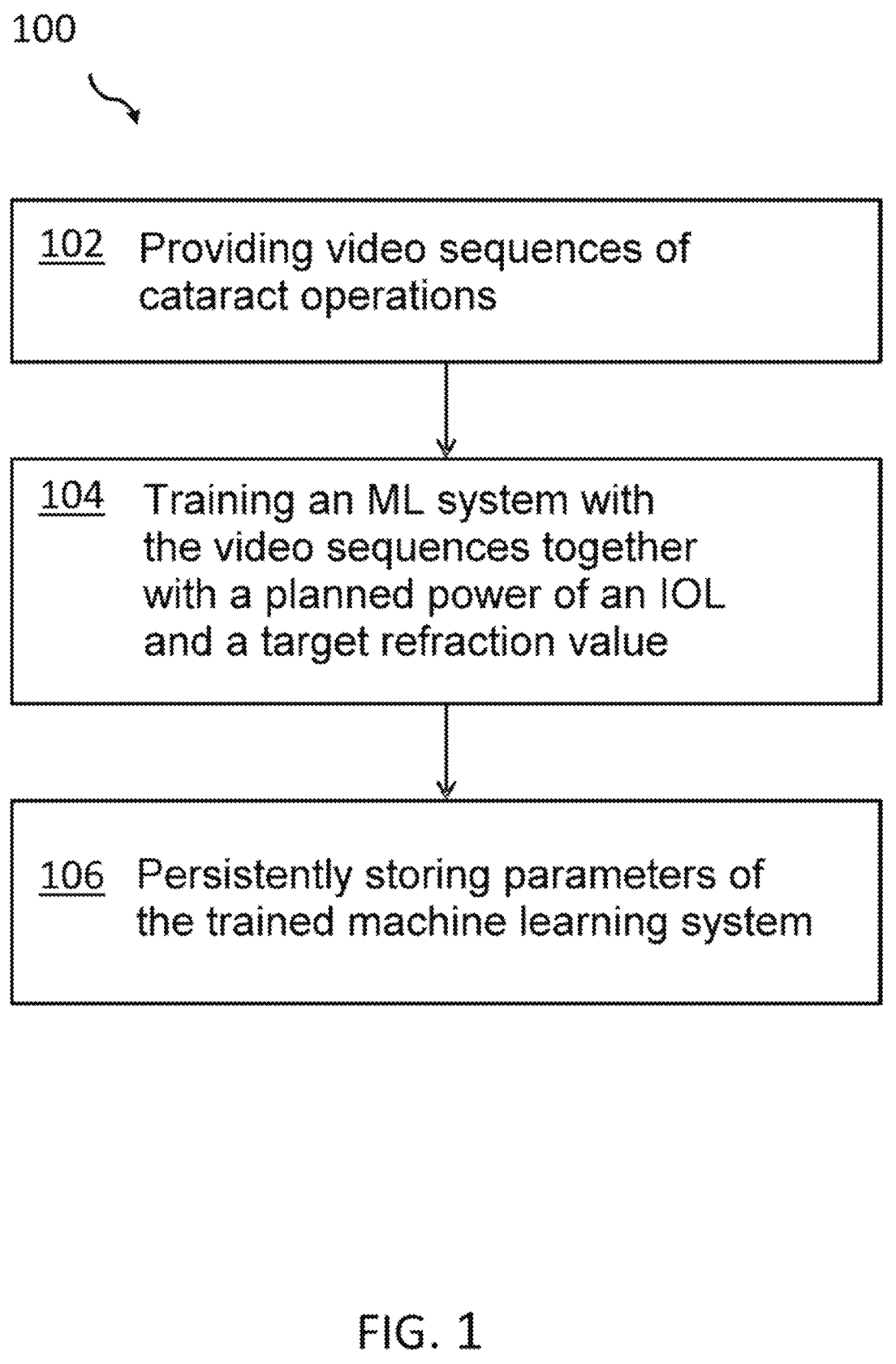

100

102    Providing video sequences of cataract operations

104    Training an ML system with the video sequences together with a planned power of an IOL and a target refraction value 106    Persistently storing parameters of the trained machine learning system

500  system

514

506  Video sequence storage unit

508  Training control system

510  Machine learning system

512  Parameter value memory

504  Memory

502  Processor

600

604

602

608 ↔ 612

610

616

606

614

500

622

618

620

AI-BASED VIDEO ANALYSIS OF CATARACT SURGERY FOR DYNAMIC ANOMALY RECOGNITION AND CORRECTION

TECHNICAL FIELD

The disclosure relates to a dynamic analysis of operations and, in particular, to a computer-implemented method for recognizing deviations from plan parameters during an ophthalmological operation, a corresponding system and a corresponding computer program product for carrying out the method.

BACKGROUND

Replacing the biological lens of an eye with an artificial intraocular lens (IOL)—for example, in the case of an (age-related) refractive error or in the case of cataracts—has become ever more common in the field of ophthalmology in recent years. In the process, the biological lens is detached from the capsular bag by way of a minimally invasive intervention and removed. The lens, which has become opacified in the case of a cataract, is then replaced by an artificial lens implant. In the process, this artificial lens implant or intraocular lens is inserted into the then empty capsular bag. Knowledge of the correct position of the intraocular lens and the necessary refractive power depend on one another.

Typically, plan parameters are attempted to be determined as part of the operation preparation in the run-up to such operations. By way of example, these include the position of the IOL in the eye following the operation and a sought effective refraction value. However, the parameter selection originally provided for the cataract operation—for example, IOL position and/or refractive power, phaco-pressure, phaco-time . . . —may no longer be the best choice for the patient during the cataract operation on account of complications arising. For the specific example of the IOL refractive power, this may arise, for example, as a result of differences in the capsulorhexis or a cornea that has been altered in terms of its refraction as a result of incisions. As a result, there may be a "nasty surprise" (a so-called "refraction surprise") for the patient following the operation.

The prior art already contains a document in this context: GONZÁLEZ, David Carmona; BAUTISTA, Carlos Palomino. Accuracy of a new intraocular lens power calculation method based on artificial intelligence. Eye, 2021, Vol. 35, No. 2, pp. 517-522. DOI: https.//doi org/10.1038/s41433-020-0883-3. The study described therein is concerned with the development and assessment of the accuracy of a refractive power calculation for a new intraocular lens using machine learning techniques. Data of patients who have had cataract surgery are used as a basis.

To minimize or even entirely prevent such surprising effects following the operation, it would therefore be desirable to use additional data that arise during the operation in order to obtain an operation result that is as optimal as possible.

SUMMARY

This advantage is achieved by the method proposed here, the corresponding system and the associated computer program product in accordance with the independent claims. Further embodiments are described by the respective dependent claims.

According to one aspect of the present disclosure, a computer-implemented method is presented for recognizing deviations from plan parameters or plan parameter values during an ophthalmological operation. The method includes a provision of video sequences of cataract operations, the video sequences having been recorded by means of an image recording apparatus, and a training of a machine learning system using the video sequences provided and also, in each case, a planned refractive power of an intraocular lens to be inserted during a cataract operation and a target refraction value following the cataract operations as training input data and associated prediction results in the form of actual refraction values following the cataract operation to form a machine learning model for predicting the actual refraction value following the cataract operation.

Furthermore, the method includes a persistent storage of parameter values of the trained machine learning system.

According to another aspect of the present disclosure, an operation assistance system is presented for recognizing deviations from plan parameters or plan parameter values during an ophthalmological operation. The operation assistance system comprises a memory that stores program code and one or more processors that are connected to the memory and that, when they execute the program code, prompt the operation assistance system to control the following units' a video sequence storage apparatus for providing video sequences of cataract operations, the video sequences having been recorded by means of an image recording apparatus; a training control system for training a machine learning system using the video sequences provided and also, in each case, a planned refractive power of an intraocular lens to be inserted during a cataract operation and a target refraction value following the cataract operation as training input data and associated prediction results in the form of an actual refraction value following the cataract operation to form a machine learning model for predicting the actual refraction value following the cataract operation; and a parameter value memory for persistently storing parameter values of the trained machine learning system.

Moreover, embodiments may relate to a computer program product able to be accessed from a computer-usable or computer-readable medium that contains program code for use by, or in connection with, a computer or any other instruction execution systems. In the context of this description, a computer-usable or computer-readable medium can be any apparatus that is suitable for storing, communicating, transmitting, or transporting the program code.

The computer-implemented method for recognizing deviations from plan parameters during an ophthalmological operation has a plurality of advantages and technical effects which may also apply accordingly to the associated system:

A use of dynamic data in the form of a sequence of digital images—i.e., a video sequence—that arises during an operation may contribute significantly to the success of the operation. The surgeon may receive further information during the operation that was not available even in the case of optimally prepared cataract operations.

In this way, it is possible to avoid uncertainty or surprisingly occurring complications during cataract operations. This would compensate for deviations from originally envisaged parameter values, which were found during the operation to no longer be the best choice for the patient. Accordingly, the patient would be spared a "nasty surprise" ("refractive surprise") following the operation.

Preoperative or intraoperative OCT data can be further input parameters that influence the choice of IOL parameters. As a result, the use of multimodal data for the prediction (i.e., video, OCT, . . . ) is rendered possible. Moreover, the parameter values of the phaco-machine can likewise be used as an input for the ML model as a result.

Furthermore, the surgeon may receive, directly while the operation is carried out, an indication in relation to a recommendation for changing the type of IOL to be inserted. Moreover, regions where there currently is a deviation from a standard operating procedure could be highlighted directly in the video stream (i.e., the video sequence). Moreover, it would be possible to indicate to the surgeon the required refractive power of the IOL, which might deviate from the planned refractive power, in order thus to select a different lens with an adapted refractive power during the operation. The same would optionally apply to a lens type of the IOL to be inserted.

Further exemplary embodiments are presented below, which can have validity both in conjunction with the method and in conjunction with the corresponding system.

According to an advantageous embodiment of the method, additional input data for the machine learning system to be trained can be used for training the machine learning system to form the machine learning model, the additional input data including at least one item selected from the group consisting of the following: ophthalmological measurement data before the ophthalmological operation on an eye to be operated on and a shape of the intraocular lens to be inserted. Additionally, further plan parameters could be used as input data for the training. What is also applicable here, in principle, is that the more data are used and available, the more usable and the closer to reality the obtainable results are. By way of example, the ophthalmological measurement data may be obtained by an A-scan or a B-scan, or may also be en face OCT data.

According to another advantageous embodiment of the method, the machine learning system can be a recurrent neural network. A neural network structured thus is particularly suitable for analysing time-varying input data, for example like in the case of the digital frames of a video sequence.

According to a developed embodiment of the method, the machine learning system can be a 3-D convolutional neural network. This type of neural network is particularly well suited to the use of raw data, for example in the form of a sequence of digital images (video sequence), and can consider both spatial and temporal dimensions when carrying out 3-D convolutions, with the movement information being encoded in a plurality of adjacent frames.

According to an additionally advantageous embodiment of the method, the latter may additionally include recording a video sequence by means of an image recording apparatus during a current cataract operation, and dynamically predicting the actual refraction value following the current cataract operation using the trained machine learning system. In this case, the recorded video sequence of the current cataract operation can be continuously and dynamically supplied to the trained machine learning system as input data. Additionally, a current target refraction value and a current planned refractive power of an intraocular lens to be inserted can be used as further input data for the trained machine learning system.

In this phase, the already trained machine learning system can be actively employed during a cataract operation in order to assist the surgeon. This component of the method could also be understood to be separate from the method according to the first aspect, which was described further above. The connecting element would be represented by the model of the machine learning system which could be used autonomously, independently (in space and time) from its actual training, with the machine learning model being used as a basis. This would also be advantageous in that more powerful computer systems could be used for the training, which may require significantly more computing power than in a subsequent inference phase. Using this, the training and active use of the underlying operation assistance system could be separated from one another both logically and physically.

Furthermore, further ophthalmological parameter values of the eye may also be used here as input data for the machine learning system. It would be advantageous for such parameter values to also have been used during the training phase of the machine learning system.

Moreover, reference is made to the fact that the image recording apparatus in this phase of the method may differ from the image recording apparatus during the training phase. This is based on the fact that the training phase and the operative phase—i.e., the inference phase—may be separated both in time and space.

According to a supplementary embodiment of the method, further additional input data can be used for the trained machine learning system for the dynamic prediction of the actual refraction value following the current cataract operation, the further additional input data including at least one item selected from the following group; ophthalmological measurement data of an eye to be operated on before the ophthalmological operation and a shape of the intraocular lens to be inserted. Ideally, values for these additional parameters would also be used as input data during the training such that the influence thereof could be taken into account in the machine learning model. This applies both to the specified plan parameters as additional input data and to any further plan parameters and their values.

Moreover, by way of the operation assistance system, the method can allow specific indication during the operation of the basis for a prediction/recommendation (explainable AI), for example by: a direct display in the visual field of the surgeon, a text-based description, a specification of the prediction confidence and a specification of how far the current course of the operation deviates from a given standard, etc.

According to a supplementarily developed embodiment of the method, the latter may additionally include at least one method step which is selected from the group which consists of determining a refraction deviation value from the planned refractive power of the intraocular lens to be inserted and the predicted actual refraction value following the current cataract operation, and dynamically determining a new refractive power of the intraocular lens to be inserted during a cataract operation.

Furthermore, it would be possible to elegantly visualize at least one value selected from the group consisting of the planned refractive power of the intraocular lens to be inserted, the target refraction value, the refraction deviation value, the new refractive power of the intraocular lens to be inserted, and a shape of the intraocular lens to be inserted, and thus assist the surgeon with their work.

Should the refraction deviation value equal zero, the new refractive power (power) of the intraocular lens to be inserted would deviate from the planned refractive power. In this way, it would be possible to signal to the surgeon to select a different lens with a different refractive power during the operation. This could also apply to the type of intraocular lens to be inserted. All these values could be overlaid into the field of view of a surgical microscope or a surgery monitor, for example, or could be displayed separately in a different way.

According to another elegant embodiment of the method, a type of cataract operation can be used as additional input value during the training to form a learning model and/or during the dynamic prediction of the actual refraction value. In appropriate exemplary embodiments, the type of cataract operation may relate to—in addition to others—the type of phacoemulsificabon, whether a Yamane technique is employed, whether this relates to an insertion of an anterior chamber intraocular lens or whether this relates to a fixation of the intraocular lens in the sulcus. Depending on the type of cataract operation, specific patterns may be retrieved from the video sequences, which then indicate peculiarities—e.g., anomalies—of the current course of the operation, or so that correspondingly deviating predictions are implemented by the machine learning system.

According to another elegant embodiment of the method, the machine learning system can be pre-trained. This would be advantageous in that the actual training time could be reduced. Optionally, fewer training data may be required as well. The data for the pre-training may be machine generated and/or be based on a physical model. All that would still be necessary during the actual, preferably shortened training with real, clinical, ophthalmological data is a fine tuning of the already pre-trained machine learning model.

According to a further embodiment of the method, the intraocular lens to be inserted can be a spherical, toric or multifocal intraocular lens to be inserted. This may relate both to the planned intraocular lens to be inserted and to the prediction by the machine learning system or its model.

According to a further developed embodiment of the method, the trained machine learning system can be an explaining machine learning system (explaining artificial intelligence). As a result of the prediction (inference) processes or parts thereof being visualized, it is possible to display to the observer—e.g., the surgeon—the input values—e.g., even within the recorded video sequences—on which the prediction is based, or which input values have had the most influence on the prediction value. A possible method to be used to this end would be, e.g., the class activation mapping, in which a type of heat map, which can highlight the areas important to the decision, is used in the image for the distinction between anomaly and normal sequence of events per frame.

DESCRIPTION OF DRAWINGS

It is pointed out that exemplary embodiments of the disclosure may be described with reference to different implementation categories. Some exemplary embodiments are in particular described with reference to a method, whereas other exemplary embodiments may be described in the context of corresponding apparatuses. Regardless of this, it is possible for a person skilled in the art to identify and to combine possible combinations of the features of the method and also possible combinations of features with the corresponding system from the description above and below—if not specified otherwise—even if these belong to different claims categories.

Aspects already described above and additional aspects of the present disclosure become apparent inter alia from the exemplary embodiments that are described and from the additional further specific refinements described with reference to the figures.

Preferred exemplary embodiments of the present disclosure are described by way of example and with reference to the following figures:

FIG. 1 depicts a flowchart-like representation of an exemplary embodiment of the computer-implemented method for recognizing deviations from plan parameters during an ophthalmological operation.

Figure 2:

FIG. 2 depicts an eye together with different biometric parameters of the eye.

Figure 3:
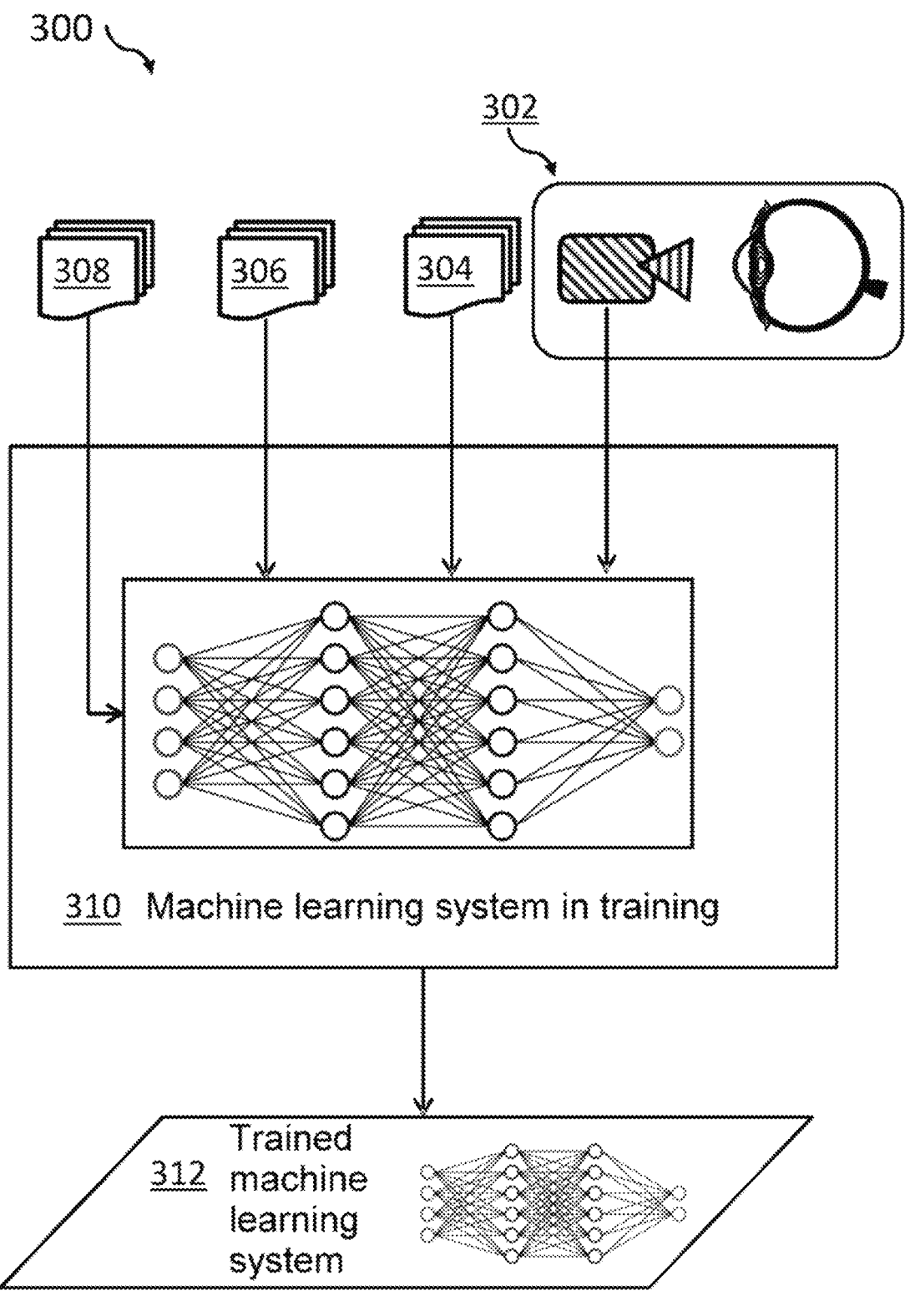

FIG. 3 depicts a schematic structure of essential functional components of the underlying proposed method or the associated system.

Figure 4:
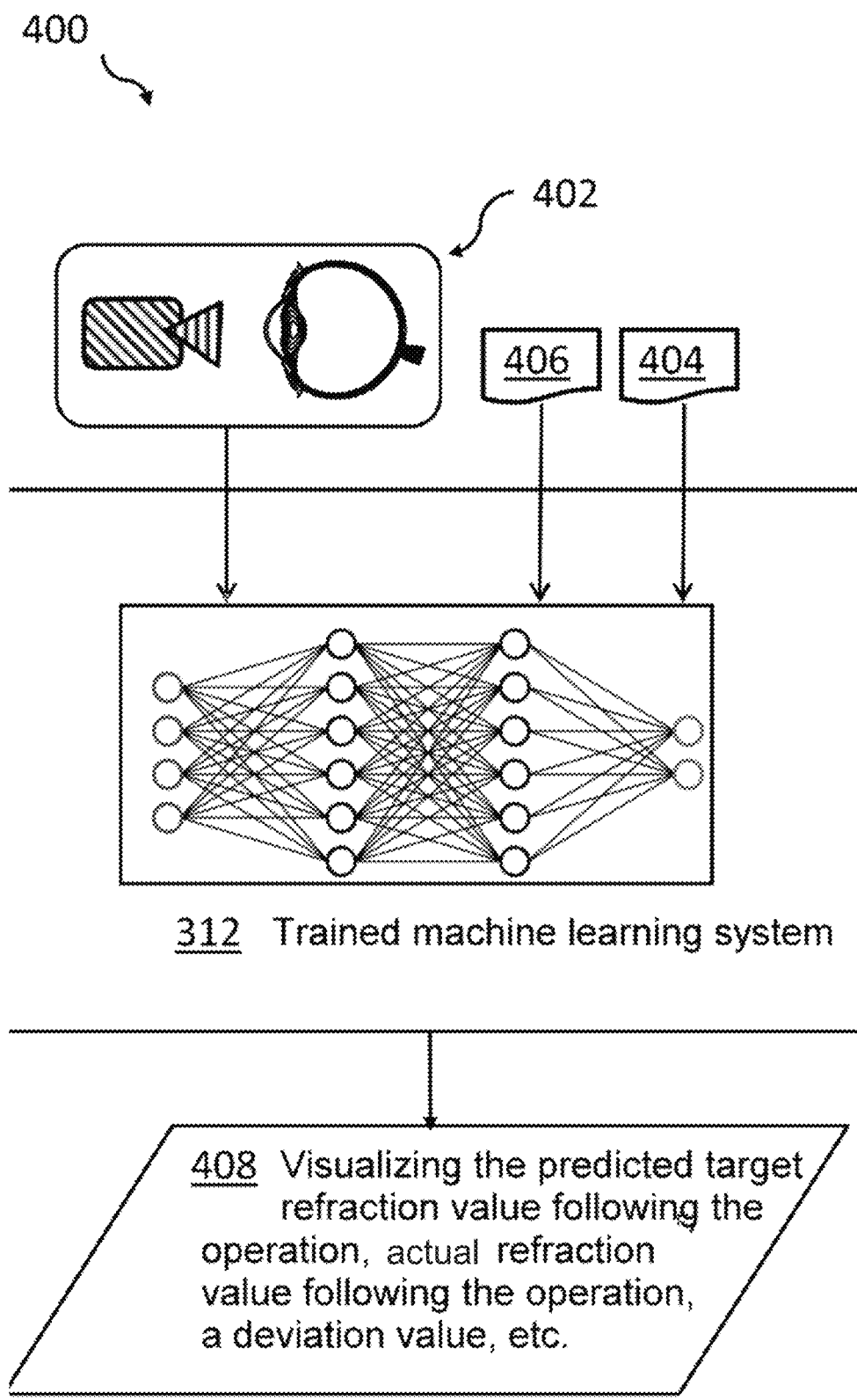

FIG. 4 depicts a diagram with components for the operation of the machine learning system.

Figure 5:
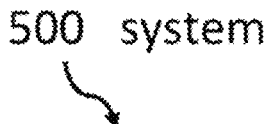

FIG. 5 depicts a diagram of the operation assistance system according to the disclosure.

Figure 6:

FIG. 6 depicts a diagram of a computer system which may additionally comprise the system according to FIG. 5 in full or in part.

DETAILED DESCRIPTION

In the context of this description, conventions, terms and/or expressions should be understood as follows.

The term "intraocular lens" describes an artificial lens which can be inserted into the eye of a patient by surgery to replace the natural, biological lens.

The term "machine learning system" describes a system that is also typically assigned to a method, said system learning from examples. To this end, annotated training data (i.e., also containing metadata) is fed to the machine learning system in order to predict output values—output classes in the case of a classification system—that were already set in advance. If the output classes are correctly output with sufficient precision—i.e., an error rate determined in advance—the machine learning system is referred to as trained. Different machine learning systems are known. These include neural networks, convolutional neural networks (CNN) or else recurrent neural networks (RNN).

In principle, the term "machine learning" is a basic term or a basic function from the field of artificial intelligence, wherein statistical methods, for example, are used to give computer systems the ability to "learn". By way of example, certain behavioural patterns within a specific task range are optimized in this case. The methods that are used give trained machine learning systems the ability to analyse data without requiring explicit procedural programming for this purpose. Typically, an NN (neural network) or CNN (convolutional neural network), for example, are examples of systems for machine learning, for forming a network of nodes which act as artificial neurons, and artificial connections between the artificial neurons (so-called links), wherein parameters (e.g., weighting parameters for the link) can be assigned to the artificial links. Activation functions can be active in the nodes. During the training of the neural network, the weighting parameter values of the links automatically adapt on the basis of input signals for the purposes of generating a desired result. In the case of supervised learning—as is the case here—the digital images in the form of video sequences supplied as input values (training data) and other input data—in general (input) data—are complemented by desired output data in the form of annotations (i.e., so-called ground-truth data), in order to generate a desired output value (desired class)—in this case, for example, a prediction for the actual refraction value following the cataract operation. Considered very generally, mapping of input data onto output data is learned.

The term "neural network" describes a network made of electronically realized nodes with one or more inputs and one or more outputs for carrying out calculation operations (activation functions). Here, selected nodes are interconnected by means of connections—so-called links or edges. The connections can have certain attributes, for example weighting parameter values, by means of which output values of preceding nodes can be influenced.

Neural networks are typically constructed in a plurality of layers. At least an input layer, a hidden layer, and an output layer are present. In a simple example, image data—e.g., frames of a video sequence—can be supplied to the input layer and the output layer can have classification results in respect of the image data—or further input parameter values. However, typical neural networks have a large number of hidden layers. The way in which the nodes are connected by links depends on the type of the respective neural network. In the present example, the prediction value of the neural learning system may be the actual refraction value of the eye with the inserted IOL following the cataract operation.

The term "recurrent neural network" denotes neural networks which, in contrast to the feed-forward networks, are distinguished by links of neurons (i.e., nodes) of one layer to neurons of the same or a preceding layer. This is the preferred manner of interconnection of neural networks in the brain, in particular in the neocortex. In artificial neural networks, recurrent connections of model neurons are frequently used to discover time-encoded—i.e., dynamic—information in the data. Examples of such recurrent neural networks include the Elman network, the Jordan network, the Hopfield network and the fully connected neural network. They are also suitable for examining a dynamic behaviour in recordings of eyes, in particular for taking account of the accommodation behaviour of the eye.

The term "parameter value"—in particular of an eye—describes geometric or biometric values, or ophthalmological data of an eye of a patient. Examples of parameter values of an eye are explained in more detail below on the basis of FIG. 2.

The term "scan result" describes digital data, for example on the basis of digital images/recordings, which represent the result of an OCT (optical coherence tomography) examination on an eye of a patient.

The term "optical coherence tomography" (abbreviated OCT) describes a known imaging method of ophthalmology, for obtaining two- and three-dimensional recordings (2-D or 3-D) of scattering materials (e.g., biological tissue) with micrometre resolution. In the process, use is essentially made of a light source, a beam splitter and a sensor—for example in the form of a digital image sensor. In ophthalmology. OCT is used to detect spatial differences in the reflection behaviour of individual retinal layers, and morphological structures can be represented with a high resolution.

The term "A-scan" (also referred to as axial depth scan) describes a one-dimensional result of a scan of a patient's eye, which provides information about geometric dimensions and locations of structures within the eye.

The term "B-scan" describes a lateral overlay of a plurality of the aforementioned A-scans, to obtain a section through the eye. Volume views are also generable by combining a plurality of layers of the eye generated thus.

The term "en face OCT" in this case describes a method for producing transverse sectional images of the eye—in contrast to longitudinal sectional images using the aforementioned A- or B-scans.

The term "digital image"—e.g., from a scan—in this case describes an image representation of, or the result of generating an amount of data in the form of pixel data from, a physically existing article: by way of example, a retina of an eye in this case. More generally, a "digital image" can be understood to be a two-dimensional signal matrix. The individual vectors of the matrix can also be adjoined to one another in order thus to generate an input vector for a layer of a CNN. The digital images can also be individual frames of video sequences—i.e., video streams.

The term "training data" describes data that can be used to train the machine learning system. In this case, these training data for the machine learning system are video sequences of operations and optionally further parameter values of the eye, for example ophthalmological data and associated refractive power values or actual refraction values following the cataract operation of earlier, successful lens exchange operations.

The term "refractive power of an intraocular lens" describes the index of refraction of the IOL.

The term "hyperparameter"—in particular of a machine learning system such as, e.g., a neural network—describes, inter alia, the architecture of the machine learning system. This may include the basic structure of the network—i.e., the architecture or the topology of the network—and further internal parameters which are not altered by the training of the machine learning system, i.e., in particular, the number of layers, the number of nodes per layer and the utilized activation functions per node. Hyperparameters of this type would be referred to as model hyperparameters. Hyperparameters of another type would be algorithm hyperparameters which essentially relate to the training behaviour itself, that is to say, for example, the training batch size and optionally also the type of back propagation function which has an effect on the learning speed without—following the completion of the training—having an influence on the predictive behaviour of the ML system.

To clarify: In contrast thereto, the parameter values of the machine learning system are adapted during the training, that is to say for example the weighting values for the links of nodes in one layer to nodes in another layer.

A detailed description of the figures is given below. It is understood in this case that all of the details and information in the figures are illustrated schematically. What is illustrated first of all is a block diagram of one exemplary embodiment of the computer-implemented method according to the disclosure for determining the refractive power for an intraocular lens to be inserted. Further exemplary embodiments, or exemplary embodiments for the corresponding system, are described below:

FIG. 1 depicts a flowchart-like representation of an exemplary embodiment of the computer-implemented method 100 according to the disclosure for recognizing deviations from plan parameters during an ophthalmological operation. The method 100 includes a provision 102 of video sequences of cataract operations—i.e., a just carried-out operation for replacing the biological lens of the eye with an artificial lens—and a training 104 of a machine learning system using the video sequences provided and also, in each case, a planned refractive power of an intraocular lens to be inserted during a cataract operation and a target refraction value following the cataract operation as training input data and associated prediction results—i.e., the predictions—in the form of an actual refraction value following the cataract operation to form a machine learning model for predicting the actual refraction value following the cataract operation. The actual measurable refraction value following the cataract operation would be considered an annotation, label or ground truth during the training phase of the supervised training, present here, of the machine learning system for forming the learning model. In this case, the video sequences were recorded by means of an image recording apparatus. The image recording apparatus can be a surgical microscope which records and stores frames by means of a magnifying optical system and an image sensor, the sequence of said frames yielding the video sequence. Alternatively, the magnification may also be implemented in purely electronic-algorithmic fashion.

Moreover, the method 100 includes a persistent storage (106) of parameter values and, optionally, hyperparameter values of the trained machine learning system. The storage of the parameter values, the activation functions of the nodes of the neural network and further hyperparameter values which describe the actual structure of the machine learning system allow the trained neural network—or the actual machine learning model—to be used at a later time on potentially different hardware in comparison with the hardware at the time of the training for prediction operations (predictions).

FIG. 2 depicts an eye 200 with different biometric or ophthalmological parameters of an eye. In particular, the following parameters are represented: axial length 202 (AL), anterior chamber depth 204 (ACD), keratometry value 206 (K, radius), refractive power of the lens (power), lens thickness 208 (LT), central cornea thickness 210 (CCT), white-to-white distance 212 (WTW), pupil size 214 (PS), posterior chamber depth 216 (PCD), retina thickness 218 (RT). This figure serves in particular as background information for a classification of cataract operations.

FIG. 3 represents a schematic structure 300 of essential functional blocks, which are useful for the implementation of the proposed method. At the centre is the machine learning system 310 to be trained, which is trained by means of supervised learning in order to generate a learning model which can be described by parameter values and optionally hyperparameter values of the trained machine learning system. Sequences of recorded digital images—in the form of video sequences 302 that are recorded by means of a video camera—of a planned refractive power 304 (or value of the planned refractive power) of an intraocular lens to be inserted and of a target refraction value 306 following the cataract operation are used as training input values. Moreover, expected target values—in particular actual measured refractive power values 308 following the operation—for given input data—i.e., ground-truth data, annotations or labels—are made available for the training of the machine learning system.

The result of this phase would be a trained machine learning system or an associated machine learning model 312 for predicting the actual refraction value following the cataract operation.

FIG. 4 depicts a diagram 400 with components for the operation of the trained machine learning system 312. Once again, video sequences 402 are supplied as input data to the trained machine learning system 312 during the operation. Moreover, the planned refractive power 404 of the intraocular lens to be inserted and the target refraction value 406 following the cataract operation are used as further parameter values. If further parameter values—e.g., ophthalmological data of the eye—were used during the training of the machine learning system 312, corresponding additional input data should also be used here for the trained machine learning system 312.

As a result, the surgeon receives predicted data, for example in visualized form 408, consisting of at least the predicted target refraction value following the operation and the actual refraction value following the operation, and a deviation value in this respect. Moreover, a recommendation for the type of intraocular lens to be inserted and the planned type of IOL can be indicated to the surgeon. In this way, the surgeon dynamically receives additional important indications during the operation so that there are no surprising effects for the patient following the IOL insertion.

FIG. 5 depicts—for the sake of completeness—a preferred exemplary embodiment of components of the operation assistance system 500, which assist the training of the machine learning system 510 according to the proposed method 100.

The operation assistance system 500 for recognizing deviations from plan parameter values during an ophthalmological operation comprises at least one memory 504 that stores program code and one or more processors 502 that are connected to the memory 504 and that, when they execute the program code, prompt the operation assistance system 500 to control the following units: a video sequence storage apparatus 506 for providing video sequences of cataract operations, the video sequences having been recorded by means of an image recording apparatus; a training control system 508 for training a machine learning system 510 using the video sequences provided and also, in each case, a planned refractive power of an intraocular lens to be inserted during a cataract operation and a target refraction value following the cataract operation as training input data and associated prediction results in the form of an actual refraction value following the cataract operation to form a machine learning model for predicting the actual refraction value following the cataract operation, and a parameter value memory 512 for persistently storing parameter values and optionally hyperparameter values of the trained machine learning system.

Express reference is made to the fact that the modules and units—in particular the processor 502, the memory 504, the video sequence storage apparatus 506, the training control system 508, the machine learning system 510 (corresponding to 312) and the parameter value memory 512—may be connected by electrical signal lines or by way of a system-internal bus system 514 for the purposes of interchanging signals or data. The video sequence storage unit 506 and the parameter value memory 512 may use an identical storage system. Additionally, a display unit (not shown) may also be connected to the system-internal bus system 514 in order to output, display or otherwise further-process or forward the refractive power.

For practical operative use, a slightly different design of the operation assistance system would be advantageous (not shown). To this end, a processor, a memory for the program code, the trained machine learning system 312 and a display unit would be useful to display the prediction values of the machine learning system to the surgeon.

FIG. 6 illustrates a block diagram of a computer system that may have at least parts of the system for determining the refractive power. Embodiments of the concept proposed here may in principle be used together with virtually any type of computer, regardless of the platform used therein to store and/or execute program codes FIG. 6 illustrates by way of example a computer system 600 that is suitable for executing program code according to the method proposed here but may also contain the prediction system in full or in part.

The computer system 600 has a plurality of general-purpose functions. The computer system may in this case be a tablet computer, a laptop/notebook computer, another portable or mobile electronic device, a microprocessor system, a microprocessor-based system, a smartphone, a computer system with specially configured special functions or else a constituent part of a microscope system. The computer system 600 may be configured so as to execute computer system-executable instructions—such as for example program modules—that may be executed in order to implement functions of the concepts proposed here. For this purpose, the program modules may contain routines, programs, objects, components, logic, data structures etc. in order to implement particular tasks or particular abstract data types.

The components of the computer system may have the following: one or more processors or processing units 602, a storage system 604 and a bus system 606 that connects various system components, including the storage system 604, to the processor 602. The computer system 600 typically has a plurality of volatile or non-volatile storage media accessible by the computer system 600. The storage system 604 may store the data and/or instructions (commands) of the storage media in volatile form—such as for example in a RAM (random access memory) 608—in order to be executed by the processor 602. These data and instructions perform one or more functions or steps of the concept proposed here. Further components of the storage system 604 may be a permanent memory (ROM) 610 and a long-term memory 612 in which the program modules and data (reference sign 616) and also workflows may be stored.

The computer system has a number of dedicated apparatuses (keyboard 618, mouse/pointing device (not illustrated), screen 620, etc.) for communication purposes. These dedicated apparatuses may also be combined in a touch-sensitive display. An 1/O controller 614, provided separately, ensures a frictionless exchange of data with external devices. A network adapter 622 is available for communication via a local or global network (LAN, WAN, for example via the Internet). The network adapter may be accessed by other components of the computer system 600 via the bus system 606. It is understood in this case, although it is not illustrated, that other apparatuses may also be connected to the computer system 600.

At least parts of the operation assistance system 500 (cf. FIG. 5) may also be connected to the bus system 606. The operation assistance system 500 and the computer system 600 may optionally use the memories and/or the processors together.

The description of the various exemplary embodiments of the present disclosure has been given for the purpose of improved understanding, but does not serve to directly restrict the inventive concept to these exemplary embodiments. A person skilled in the art will himself develop further modifications and variations. The terminology used here has been selected so as to best describe the basic principles of the exemplary embodiments and to make them easily accessible to a person skilled in the art.

The principle proposed here may be embodied as a system, as a method, combinations thereof and/or also as a computer program product. The computer program product may in this case have one (or more) computer-readable storage medium (media) that contain(s) computer-readable program instructions in order to prompt a processor or a control system to execute various aspects of the present disclosure.

Electronic, magnetic, optical, electromagnetic or infrared media or semiconductor systems are used as forwarding medium; for example SSDs (solid state devices/drives as solid state memory), RAM (random access memory) and/or ROM (read-only memory), EEPROM (electrically erasable ROM) or any combination thereof. Propagating electromagnetic waves, electromagnetic waves in waveguides or other transmission media (for example light pulses in optical cables) or electrical signals transmitted in wires also come into consideration as forwarding media.

The computer-readable storage medium may be an embodying apparatus that retains or stores instructions for use by an instruction execution device. The computer-readable program instructions that are described here may also be downloaded onto a corresponding computer system, for example as a (smartphone) app from a service provider via a cable-based connection or a mobile radio network.

The computer-readable program instructions for executing operations of the disclosure described here may be machine-dependent or machine-independent instructions, microcode, firmware, status-defining data or any source code or object code that is written for example in C++, Java or the like or in conventional procedural programming languages such as for example the programming language "C" or similar programming languages. The computer-readable program instructions may be executed in full by a computer system. In some exemplary embodiments, it may also be electronic circuits such as for example programmable logic circuits, field-programmable gate arrays (FPGAs) or programmable logic arrays (PLAs) that execute the computer-readable program instructions by using status information of the computer-readable program instructions in order to configure or to customize the electronic circuits according to aspects of the present disclosure.

The disclosure proposed here is furthermore illustrated with reference to flowcharts and/or block diagrams of methods, apparatuses (systems) and computer program products according to exemplary embodiments of the disclosure. It is pointed out that virtually any block of the flowcharts and/or block diagrams may be designed as computer-readable program instructions.

The computer-readable program instructions may be made available to a general-purpose computer, a special computer or a data processing system able to be programmed in another way in order to create a machine such that the instructions that are executed by the processor or the computer or other programmable data processing apparatuses generate means for implementing the functions or procedures that are illustrated in the flowchart and/or block diagrams. These computer-readable program instructions may accordingly also be stored on a computer-readable storage medium.

In this sense, any block in the illustrated flowchart or the block diagrams may represent a module, a segment or portions of instructions that represent several executable instructions for implementing the specific logic function. In some exemplary embodiments, the functions that are illustrated in the individual blocks may be executed in another order, possibly also in parallel.

The illustrated structures, materials, sequences, and equivalents of all of the means and/or steps with associated functions in the claims below are intended to apply all of the structures, materials or sequences as expressed by the claims.

REFERENCE SIGNS

100 Method for recognizing deviations from plan parameters during an ophthalmological operation

13

102 Method step of 100
104 Method step of 100
106 Method step of 100
200 Eye parameters
202 Axial length
204 Anterior chamber thickness
206 Keratometry value
208 Lens thickness
210 Central cornea thickness
212 White-to-white distance
214 Pupil size
216 Posterior chamber depth
218 Retina thickness
300 Function blocks for the implementation of the method
302 Video sequences from a camera
304 Value of the planned refractive power
306 Target refraction value following the cataract opera-
tion
308 Actual measured refractive power values following
the operation
310 Machine learning system in training
312 Trained machine learning system with learning model
400 Components for the active operation of the machine
learning system
402 Video sequence(s)
404 Planned refractive power of the intraocular lens to be
inserted
406 Target refraction value
408 Output (visualization) of predicted data
500 Operation assistance system
502 Processor
504 Memory
506 Video sequence storage apparatus
508 Training control system
510 Machine learning system
512 Parameter value memory
514 Bus system
600 Computer system
602 Processor
604 Storage system
606 Bus system
608 RAM
610 ROM
612 Long-term memory
614 1/O controller
615 Program modules, potential data
618 Keyboard
620 Screen
622 Network adapter

The invention claimed is:

1. A computer-implemented method for recognizing
deviations from plan parameter values during a cataract
operation, the method comprising:
providing video sequences of cataract operations, the
video sequences having been recorded using one or
more image recording apparatuses;
training a machine learning system using as training input
data:
the video sequences, and
for each cataract operation:
a planned refractive power of an intraocular lens to
be inserted during the cataract operation;
a target refraction value following the cataract opera-
tion; and
an associated prediction result comprising an actual
refraction value following the cataract operation,

wherein the machine learning system is trained to form
a machine learning model for dynamically predict-
ing, during a cataract operation, the actual refraction
value following the cataract operation, and predict-
ing a deviation value between a target refraction
value following the cataract operation and a pre-
dicted actual refraction value following the cataract
operation; and
persistently storing parameter values of the trained
machine learning system.
2. The method of claim 1, wherein additional input data
for the machine learning system includes at least one of
ophthalmological measurement data before the cataract
operation on an eye to be operated on or a shape of the
intraocular lens to be inserted.
3. The method of claim 1, wherein the machine learning
system comprises a recurrent neural network.
4. The method of claim 1, wherein the machine learning
system comprises a 3-D convolutional neural network.
5. The method of claim 1, wherein a type of cataract
operation is used as additional training input data during the
training to form a learning model.
6. The method of claim 1, further comprising:
recording a video sequence using an image recording
apparatus during a current cataract operation; and
dynamically predicting the actual refraction value follow-
ing the current cataract operation using the trained
machine learning system, the recorded video sequence
of the current cataract operation being continuously and
dynamically supplied to the trained machine learning
system as input data, and a current target refraction
value and a current planned refractive power of an
intraocular lens to be inserted being used as further
input data for the trained machine learning system.
7. The method of claim 6, wherein additional input data
are used for the trained machine learning system for the
dynamic prediction of the actual refraction value following
the current cataract operation, the additional input data
including at least one of ophthalmological measurement data
of an eye to be operated on before the cataract operation or
a shape of the intraocular lens to be inserted.
8. The method of claim 6, further comprising:
at least one of determining a refraction deviation value
from the planned refractive power of the intraocular
lens to be inserted and the predicted actual refraction
value following the current cataract operation, or
dynamically determining a new refractive power of the
intraocular lens to be inserted during a cataract opera-
tion; and
visualizing at least one of:
the planned refractive power of the intraocular lens to
be inserted,
the target refraction value,
the refraction deviation value,
the new refractive power of the intraocular lens to be
inserted, or
a shape of the intraocular lens to be inserted.
9. The method of claim 6, wherein a type of cataract
operation is used as additional input value during the
dynamic prediction of the actual refraction value.
10. The method of claim 9, wherein the type of cataract
operation is based on phacoemulsification, employs a
Yamane technique, relates to an insertion of an anterior
chamber intraocular lens, or relates to a fixation of the
intraocular lens in the sulcus.
11. The method of claim 1, wherein the machine learning
system is pre-trained.

12. The method of claim 1, wherein the intraocular lens to be inserted comprises a spherical, toric, or multifocal intraocular lens to be inserted.

13. The method of claim 1, wherein the trained machine learning system comprises an explaining machine learning system.

14. An operation assistance system for recognizing deviations from plan parameter values during a cataract operation, the operation assistance system comprising:

memory that stores program code; and one or more processors that are connected to the memory and that, when they execute the program code, prompt the operation assistance system to control;

a video sequence storage apparatus for providing video sequences of cataract operations, the video sequences having been recorded using one or more image recording apparatuses;

a training control system for training a machine learning system using, as training input data, the video sequences and, for each cataract operation:

a planned refractive power of an intraocular lens to be inserted during the cataract operation; a target refraction value following the cataract operation; and an associated prediction result comprising an actual refraction value following the cataract operation, wherein the machine learning system is trained to form a machine learning model for dynamically predicting, during a cataract operation, the actual refraction value following the cataract operation, and predicting a deviation value between a target refraction value following the cataract operation and a predicted actual refraction value following the cataract operation; and parameter value memory for persistently storing parameter values of the trained machine learning system.

15. A computer-readable storage medium storing a computer program product for recognizing deviations from plan parameters during a cataract operation, wherein the computer program product, when executed by one or more computers or control units, cause the one or more computers or control units to perform operations comprising:

providing video sequences of cataract operations, the video sequences having been recorded using one or more image recording apparatuses, training a machine learning system using as training input data:

the video sequences, and for each cataract operation:

a planned refractive power of an intraocular lens to be inserted during the cataract operation;

a target refraction value following the cataract operation; and an associated prediction result comprising an actual refraction value following the cataract operation, wherein the machine learning system is trained to form a machine learning model for dynamically predicting, during a cataract operation, the actual refraction value following the cataract operation, and predicting a deviation value between a target refraction value following the cataract operation and a predicted actual refraction value following the cataract operation; and persistently storing parameter values of the trained machine learning system.

16. The computer-readable storage medium of claim 15, wherein additional input data for the machine learning system includes at least one of ophthalmological measurement data before the cataract operation on an eye to be operated on or a shape of the intraocular lens to be inserted.

17. The computer-readable storage medium of claim 15, wherein the machine learning system comprises a recurrent neural network.

18. The computer-readable storage medium of claim 15, wherein the machine learning system comprises a 3-D convolutional neural network.

19. The computer-readable storage medium of claim 15, wherein a type of cataract operation is used as additional training input data during the training to form a learning model.

20. The computer-readable storage medium of claim 15, wherein the operations further comprise:

recording a video sequence using an image recording apparatus during a current cataract operation; and dynamically predicting the actual refraction value following the current cataract operation using the trained machine learning system, the recorded video sequence of the current cataract operation being continuously and dynamically supplied to the trained machine learning system as input data, and a current target refraction value and a current planned refractive power of an intraocular lens to be inserted being used as further input data for the trained machine learning system.

* * * * *